United States Patent [19]
Lahille et al.

[11] Patent Number: 5,911,760
[45] Date of Patent: Jun. 15, 1999

[54] PRODUCT FOR COVERING A PROSTHESIS

[75] Inventors: Michel Lahille, Vauhallan; Mourad Ben-Mokhtar, Paris, both of France

[73] Assignee: Terolab Services-SNMC, Villeneuve le Roi, France

[21] Appl. No.: 08/689,497

[22] Filed: Aug. 7, 1996

[30] Foreign Application Priority Data

Aug. 14, 1995 [FR] France ..................................... 95-09865
Nov. 14, 1995 [FR] France ..................................... 95-13578

[51] Int. Cl.⁶ .................................. A61F 2/02; B05D 7/00
[52] U.S. Cl. ............................................ 623/66; 204/192.1
[58] Field of Search ................................. 623/11, 16, 18, 623/66; 240/191.1, 192.1

[56] References Cited

U.S. PATENT DOCUMENTS 5,013,323  5/1991  Kobayashi et al. ........................ 623/16

FOREIGN PATENT DOCUMENTS 2647334  11/1990  France .
2706308  12/1994  France .
WO9417838  8/1994  WIPO .

*Primary Examiner*—David J. Isabella
*Attorney, Agent, or Firm*—Laubscher & Laubscher

[57] ABSTRACT

The product for covering a prosthesis (1) includes calcium carbonate ($CaCO_3$), preferably in the form of calcite and smaller amounts of aragonite, and lime, mainly quick lime (CaO). The product is the result of thermal transformation of a substance containing calcite and/or argonite and/or quick lime or hydrated lime. The thermal transformation is carried out by thermal sputtering using a plasma torch in which the substance is injected in powder form into a plasma jet.

12 Claims, 2 Drawing Sheets

PRODUCT FOR COVERING A PROSTHESIS

BACKGROUND OF THE INVENTION

1. Field the Invention

The present invention concerns a biocompatible product containing calcium carbonate and used to cover at least part of a prosthesis in order to integrate the latter into the surrounding bone.

2. Description of the Prior Art

Products containing calcium carbonate are specified by Georges CAMPRASSE in French patents Nos. 2,647,334 and 2,706,308 and the patent application WO 94/17838, in particular for manufacturing shaped parts such as implants and prostheses for orthopedic surgery, or replacement dental roots. These products are made from the mother-of-pearl of aquatic molluscs, for example the mother-of-pearl of Pinctada Maxima, which is subject to a specific mechanical, thermal and chemical treatment. This specific treatment consists in applying to the mother-of-pearl part previously obtained by mechanical preparation of mollusc shells, physical-chemical operations of soaking, washing, rinsing, and steam treatment in the presence of chemical agents, followed by drying at staggered temperatures.

CAMPRASSE products can be particularly used in powder form and have adhesive properties which make them suitable for association with other materials, such as metals or organic polymers, in a biological cement for bedding any prosthesis. The products obtained in this way can be used as a coating on certain metals, rather than a covering integral with the latter, for improved adhesion to the bone tissue.

The CAMPRASSE products can also be used in a compacted form to make a prosthesis itself, for example a tibial plate, a femoral condyl, a hip prosthesis, a screw, etc.

The biocompatible properties of CAMPRASSE products are mainly the result of the composition based on calcium carbonate in the form of both calcite and aragonite. The presence of calcium carbonate in the skeleton of stony corals (order madreporaria), such as Porites, has also lead to the use of the latter, in particular in dental surgery.

CAMPRASSE products have two main drawbacks:

their animal origin makes it very difficult if not impossible to obtain approval in some countries;

their cost is high because of the mother-of-pearl from which they are obtained, which is a relatively rare material, and because of the equipment and labor required for the particular physical-chemical operations required to prepare them.

OBJECT OF THE INVENTION

The present invention is aimed at providing a product for use in the manufacture of prostheses which is entirely of mineral origin, less costly and at least as histocompatible as the products of the above prior art technique.

SUMMARY OF THE INVENTION

To this end, the prosthesis covering product includes calcium carbonate and, in accordance with the invention, lime.

As will emerge below, this product is more particularly intended to constitute a covering on the prosthesis, totally integrated with at least part of the surface of the prosthesis, by thermal deposition on the latter, as explained below. A covering of this kind that is integrated with its support, such as a prosthesis, is therefore different from and not equivalent to a coating as used by CAMPRASSE, which by virtue of its pasty consistency is applied to the prosthesis and separable therefrom.

The covering product of the invention does not include any material of organic origin, in particular animal origin, when to it is applied to the prosthesis. In the product of the invention the calcium carbonate may be in the form of calcite, preferably constituting up to 75% of the weight of the product, and/or aragonite, preferably constituting up to 25% of the weight of the product, and the lime may constitute up to 60% of In the weight of the product, the lime comprising quick lime CaO and/or hydrated lime $Ca(OH)_2$. In a different embodiment the lime in the coating product may comprise hydrated lime $Ca(OH)_2$, preferably constituting at most 25% of the weight of the product. For example, the covering product comprises 65% to 75% calcite with traces of aragonite, less than 10% of the weight of the product, and 25% to 35% quick lime with traces of hydrated lime, less than 10% of the weight of the product.

The product of the invention is histocompatible.

Radiological examination shows that the product of the invention contributes to the growth of hard bony tissue around the prosthesis, with the result that a few months after implantation of the prosthesis the product can no longer be distinguished from the surrounding bone. The prosthesis is entirely surrounded with bony tissue, unlike the fibrous tissue that usually grows around a prosthesis covered with hydroxyapatite.

The manufacture of the product containing calcium carbonate and lime and embodying the invention mainly consists in a thermal transformation of an initial substance comprising at least one of the following constituents: aragonite, calcite, quick lime and hydrated lime, into the product. More particularly, the thermal transformation is applied to either an initial substance comprising essentially, by which is meant between 95% and 100%, inclusive, of the weight of the substance: aragonite, calcite, quick lime and hydrated lime, or an initial substance comprising at least one of the constituents, aragonite and calcite, in a large amount between 10% and 90% by weight of the substance and, if necessary, lime, i.e., quick lime CaO and hydrated lime $Ca(OH)_2$ in smaller amounts, typically 5% to 50% by weight of the substance.

The following compositions of the initial substance with the following proportions have given satisfactory results, for example:

30% to 90% by weight aragonite and 10% to 70% by weight calcite,

50% to 90% by weight aragonite and 10% to 50% by weight quick lime CaO;

50% to 90% by weight calcite and 10% to 50% by weight quick lime Cao;

20% to 80% by weight aragonite, 10% to 70% by weight calcite, and 10% to 50% by weight quick lime CaO;

20% to 80% by weight aragonite, 10% to 70% by weight calcite, and 10% to 50% by weight hydrated lime $Ca(OH)_2$;

80% to 95% by weight aragonite and 5% to 20% by weight hydrated lime $Ca(OH)_2$; and 80% to 95% by weight calcite and 5% to 20% by weight hydrated lime $Ca(OH)_2$.

The four main constituents mentioned above, i.e., aragonite, calcite, quick lime and hydrated lime, together constituting at least some 50% of the substance, are all of mineral origin, which substantially reduces the cost of the raw material from which the product of the invention is made, compared to the mother-of-pearl of animal origin specified for the CAMPRASSE product. The cost reduction is around 80% to 90%. Calcite, also known as Iceland spar, the rhombohedric form of calcium carbonate, is very widespread in the natural state in marbles, chalk, etc. ; likewise aragonite, the orthorhombic form of crystalline calcium carbonate. The lime, whether in the form of quick lime CaO, also known as calcium oxide, or in the form of hydrated lime $Ca(OH)_2$, also known as dead lime or Portlandite, is an ordinary commercial substance manufactured in large quantities.

The thermal transformation of the substance is carried out at temperatures near the melting point of calcium, which is equal to 839° C., i.e. at temperatures between 750° C. and 900° C., so that a proportion of the calcite is converted into lime, releasing carbon dioxide, and, if necessary, into a lower proportion of aragonite which it at least partly converted into calcite at intermediate temperatures of around 480° C. Where the hydrated lime $Ca(OH)_2$ is provided in the initial substance, it is converted into quick lime CaO by the elimination of water on heating the substance. For these reasons, the proportion of calcite in the initial substance is generally lower than that in the final prosthesis covering product of the invention and the proportion of quick lime, if any, in the initial substance may be lower than that in the final prosthesis covering product.

The various proportions of the constituents in the final covering product depend in particular on the constituents selected and on their proportions in the initial product, as well as on the mechanical characteristics of the initial product and the characteristics of the heat treatment of the substance.

The following substances and particular proportions of constituents may be selected to form a substance from which a covering product of the invention is obtained, for example:

1) 30% or 90% aragonite and 70% or 10% calcite, respectively;

2) 50% aragonite or calcite with 50% quick lime CaO; or 90% aragonite or calcite with 10% quick lime CaO;

3) 80% aragonite, 10% calcite and 10% quick lime; or 20% aragonite, 70% calcite and 10% quick lime; or 30% aragonite, 20% calcite and 50% quick lime;

4) 90% aragonite or calcite with 10% hydrated lime $Ca(OH)_2$.

For some applications the initial substance may be enriched with alumina $Al_2O_3$, preferably 5% to 50% by weight alumina.

The thermal transformation of the substance is preferably carried out by thermal sputtering of the substance to cover at least part of a prosthesis with said product. The thermal sputtering is performed by means of a plasma jet into which the substance is introduced in powder form, or into which the constituents of the substance are introduced separately in powder form.

BRIEF DESCRIPTION OF THE DRAWINGS

The foregoing and other objects, features and advantages of the invention will be apparent from the following detailed description of several embodiments of the invention with reference to the corresponding accompanying drawings in which.

DESCRIPTION OF THE PREFERRED EMBODIMENTS

Figure 1:
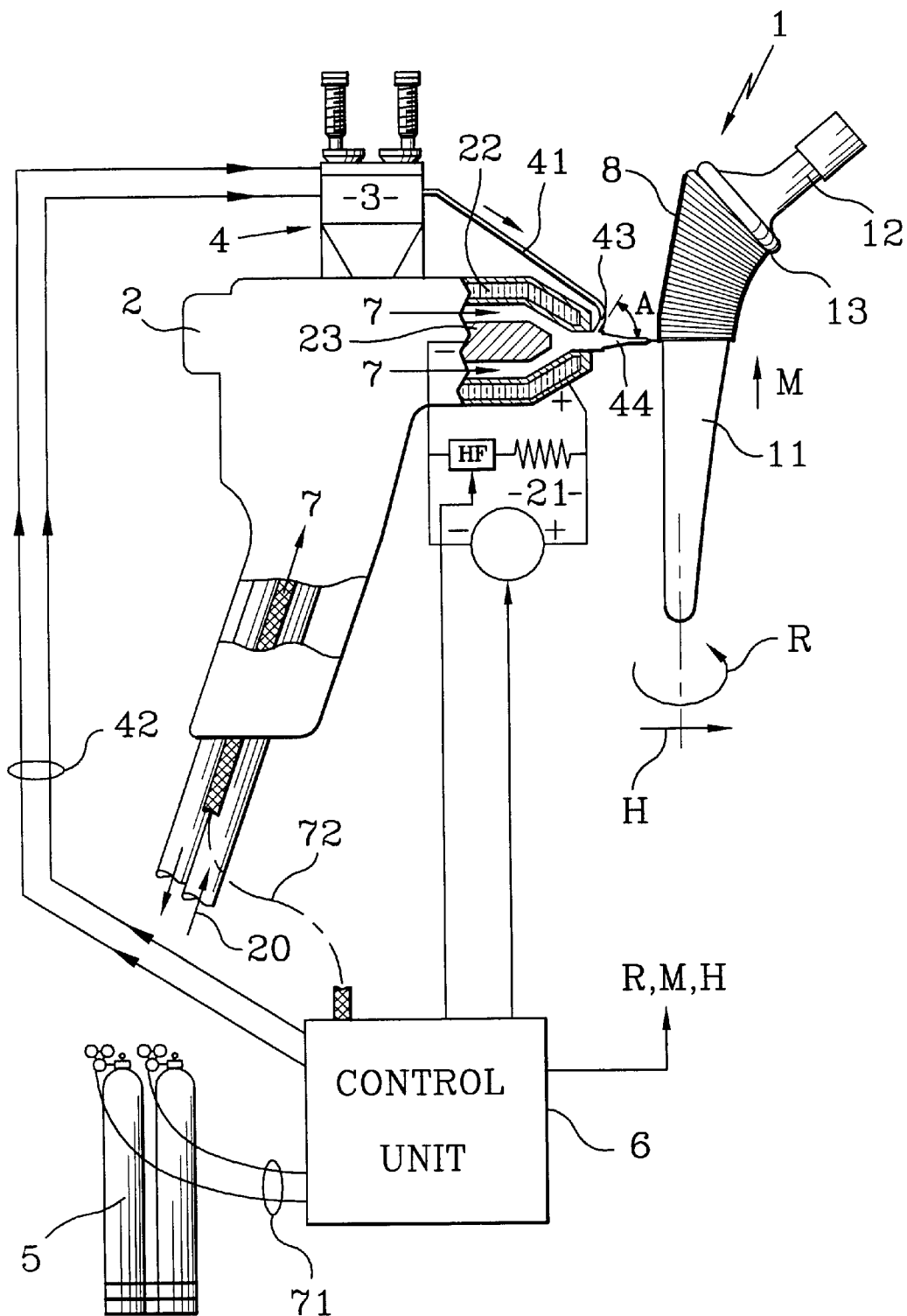
FIG. 1 is a diagram showing by way of non-limiting example an installation for covering prostheses by thermal sputtering with a plasma torch head employing external injection of powder of substance in a first embodiment, for carrying out the method of manufacturing the product of the invention.

The thermal sputtering of the substance onto a prosthesis 1, such as the femoral shank of a hip prosthesis, is an atmospheric plasma-generating sputtering operation using a plasma torch 2 cooled by water 20, as shown in FIG. 1. In the torch the substance 3 in powder form is injected from a powder dispenser 4 through a pressurized powder pipe 41 into a strongly exothermic plasma jet 44 and acquires high kinetic energy so that it is sprayed and deposited onto the surface of the prosthesis 1. The plasma torch 2 is connected to a store of cylinders 5 equipped with flowmeters and containing gases such as argon and/or nitrogen and other additive gases such as hydrogen and/or helium. The gas mixture can be a mixture of:

argon and hydrogen, or nitrogen and helium, or argon and nitrogen, or argon, hydrogen and helium.

A control unit 6 is connected by pipes 71 to the store 5 to control the proportions of the gases and their flowrate in a predetermined gas mixture 7 fed to the torch via a pipe 72.

The control unit 6 also controls voltage sources including a high-frequency source 21 of the torch 2 and also slaves the flowrate of the powdered substance 3 in the powder dispenser 4 via electrical and pneumatic connections 42 according to the deposit of covering product required.

In the embodiment shown in FIG. 1, the injection of powder is external to an anode nozzle 22. In the head of the torch 2, a powder injection end 43 of a powder pipe 41 opens in front of the anode nozzle 22 through which passes an ionized gas at high temperature produced from the gas mixture 7. The injection end 43 of the powder pipe 41 is preferably oriented towards the interior of the torch 2, in the opposite direction to the plasma jet, and inclined at an angle A between about 45° and about 90°. Because of this inclination the powdered substance penetrates more deeply and centrally into the plasma jet 44 and is better distributed at the center of the latter, which makes the heat treatment of the powder grains uniform.

Figure 2:
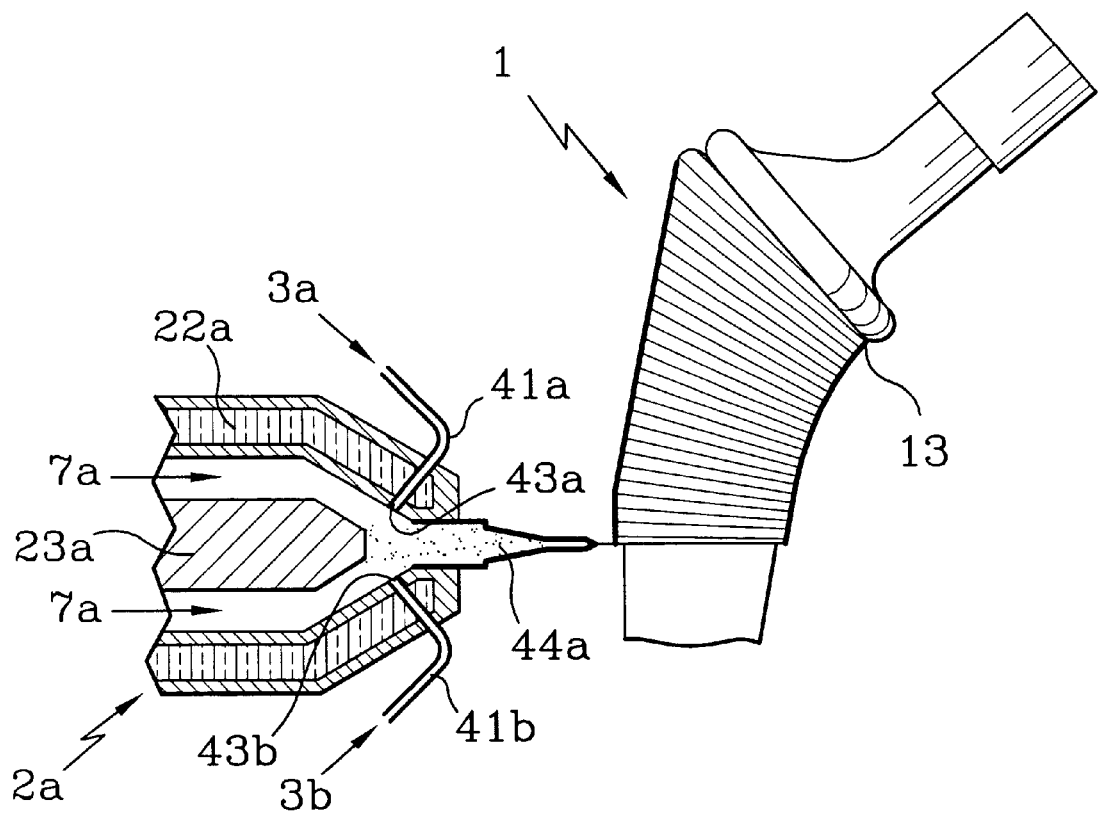
FIG. 2 shows a detailed cross-section view of the head of a plasma torch with separate internal injection of constituent powders, in a second embodiment of the method.

In a different embodiment, shown in FIG. 2, instead of the injection of powder 1 being external, the injection of powder is internal to the anode. The injection orifice 43a of a powder pipe 41a discharges in front of the anode nozzle 22a inside the torch 2a, in front of the cathode 23a and into the gas mixture injection pipe 7a. This embodiment has the advantages of increasing the concentration of powder in the hot central areas of the plasma jet 44a and of entraining all the powder grains at the velocity of the plasma jet.

The morphology, purity and particle size range of the powder injected into the plasma jet are selected according to the characteristics of the required covering product and the sputtering efficiency.

The powders of the constituents that constitute the initial powder substance are not usable in the unprocessed state in which they are delivered. The thermal sputtering is more efficient if the granules constituting the powders are pure, spheroidal and fine. The powders of the constituents are initially purified of organic products and other impurities. This purification is effected by means of heat treatment of the powders, typically at 300° C. to 400° C., before injection of the powders, or by their subsequent passage into the plasma jet.

The spheroidization is preferably achieved by atomizing the powders. This entails preparing a mixture of the powders in the form of a slip and then atomizing the granules of the slip into spherical powder particles. The slip is a relatively liquid pasty mass produced by mixing the powders with distilled water, flocculating agents to prevent the powder clumping, and a binder such as polyvinyl alcohol. The powder substance obtained in this way preferably has a range of particle sizes between 10 μm and 250 μm.

Where the substance to be injected comprises several powders, the powders can be mixed:

either before atomization, the mixture being subsequently atomized and injected via a single pipe 41 as described above and shown in FIG. 1;

or after separate atomizations of the powder of the constituents into pasty masses 3a, 3b, . . . and separate injections of the pasty masses via respective injection orifices 43a, 43b, . . . of pipes 41a, 41b, . . . connected to respective feed tanks, as shown by way of example in FIG. 2, the granules injected being mixed on entering the plasma jet 44a in this case.

In the embodiment shown in FIG. 1, the plasma torch is fixed and the output of the torch head directs a horizontal plasma jet 44 towards the surface of the prosthesis to be covered with the product 8 of the invention. The plasma torch 2 operates with an internal arc, also known as a transferred arc, which means that no current is conducted by the plasma jet 44 to the outside in front of the anode nozzle 22. In a different embodiment the plasma torch operates with an external arc and the current flows through all of the plasma jet as far as the prosthesis 2 to be covered which is positively polarized and serves as an external anode.

As shown diagrammatically in FIG. 1, the prosthesis 1 is mounted on a mandrel of a plate. The plate is preferably that of a micrometer table that moves the prosthesis by a predetermined amount in three dimensions, for example comprising in combination a rotation R about a vertical axis, an upward translation movement M and a horizontal translation movement H. This predetermined displacement R, M, H of the prosthesis relative to the plasma torch, or of the plasma torch relative to the prosthesis which is fixed or moved with only one or two of the movements R, M, H in other embodiments, is obtained by programming the control unit 6 that controls motors of the micrometer table so that the plasma jet 44 sweeps the surface of the prosthesis onto which the product 8 of the invention must be deposited. The head of the torch 2 is moved a few centimeters away from the prosthesis 1 so that the powder particles are deposited onto the surface of the prosthesis at a temperature between about 750° C. and 950° C., selected in accordance with the selected compositions and proportions of the powder mixture and the plasma-generating mixture and thus on the composition of the deposit of the product 8 finally obtained.

In the embodiment shown the prosthesis 1 is a hip prosthesis the major part of which, the prosthetic shank 11, must be covered by the covering product 8 of the invention. The upper proximal part of the prosthesis, mainly comprising a neck 12 adapted to receive a prosthetic cotyl and a flange 13, do not have the product deposited on them.

The covering product can be deposited in a single layer 10 μm to 100 μm thick by rotating the prosthesis about a vertical axis and raising (or lowering) it and moving it progressively in horizontal translation. The deposition time for a prosthesis of this kind is approximately a few minutes to deposit 10 grams to 20 grams of the covering product 8 of the invention.

Depending on the type of prosthesis and applicable regulations, those concerning contamination in particular, the sputtering and deposition operation can be carried out in a vacuum enclosure or in a controlled atmosphere enclosure. Instead of a plasma torch, the thermal sputtering can be carried out using a discontinuous gun, also known as a detonation cannon, in which the powder constituents are introduced or the powder substance is introduced into a combustion chamber and is ejected periodically by explosions.

Although the prosthesis shown in FIG. 1 is a hip prosthesis, the covering product of the invention may be thermally deposited onto other metal or ceramic (in particular titanium or alumina) prostheses and implants, to facilitate bone growth. These prostheses and implants can be, for example, screws, rods and plates for osteosynthesis, intervertebral cages or spacers, osteotomy wedges, prosthetic rods and/or shanks and/or cotyls for joints such as hip, knee, shoulder, finger. The prosthetic covering product can be deposited on the outside surface of these prostheses or implants and on the inside walls of holes or cavities formed in the prostheses and implants.

What we claim is:

1. A method for coating a prosthesis, comprising:

depositing by thermal sputtering on the prosthesis by means of a plasma torch a substance including at least one constituent selected from the group consisting of argonite, calcite, quick lime, and hydrated lime.

2. A method for coating a prosthesis as defined in claim 1, wherein said substance is a mineral substance in powder form, and further including the preliminary step of atomizing said mineral powder substance with distilled water to form a pasty mass, and injecting said pasty mass into said plasma torch.

3. A method for coating a prosthesis as defined in claim 2, wherein a plurality of batches of said mineral powder substance pasty mass are simultaneously injected into said plasma torch.

4. A method for coating a prosthesis as defined in claim 2, and further including the preliminary step of purifying said mineral powder substance by heat treatment at a temperature of between 300° C. and 400° C.

5. A method for coating a prosthesis as defined in claim 1, wherein said substance is injected in opposed relation to said plasma torch at an angle of inclination between about 45° to about 90° relative to the axis of the plasma torch.

6. A method for coating a prosthesis as defined in claim 1, wherein batches of said at least one constituent are injected substantially in opposition to said plasma torch at an angle of inclination of between about 45° and about 90° relative to the axis of the plasma torch.

7. A method for coating a prosthesis as defined in claim 1, wherein said plasma torch is made up of a plasma-generating gas selected from the group consisting of argon and hydrogen, nitrogen and helium, argon and nitrogen, and argon, hydrogen, and helium.

8. A method for coating a prosthesis as defined in claim 1, wherein said plasma jet is displaced relative to the prosthesis during the thermal deposition of the coating on the prosthesis.

9. A method for coating a prosthesis as defined in claim 1, wherein said coating has a thickness less than about 100 $\mu$m.

10. A method for coating a prosthesis as defined in claim 1, wherein the substance is thermally deposited on the prosthesis at a temperature of from between about 750° C. and about 900° C.

11. A method for coating a prosthesis as defined in claim 1, wherein said substance further includes alumina.

12. A coated prosthesis produced by the method defined in claim 1.

* * * * *